United States Patent [19]
Watanabe et al.

[11] Patent Number: 6,140,105
[45] Date of Patent: Oct. 31, 2000

[54] CELLULOSE-PRODUCING BACTERIA

[75] Inventors: Kunihiko Watanabe, Kawasaki; Hiroshi Takemura, Handa; Mari Tabuchi, Kawasaki; Naoki Tahara, Kawasaki; Hiroshi Toyosaki, Kawasaki; Yasushi Morinaga, Kawasaki; Takayasu Tsuchida, Kawasaki; Hisato Yano, Kawasaki; Fumihiro Yoshinaga, Kawasaki, all of Japan

[73] Assignee: Bio-Polymer Research Co., Ltd., Kawasaki, Japan

[21] Appl. No.: 09/359,812

[22] Filed: Jul. 23, 1999

Related U.S. Application Data

[62] Division of application No. 08/930,587, Jan. 9, 1998, Pat. No. 5,962,277, and a division of application No. PCT/JP96/00481, Feb. 29, 1996.

[30]    Foreign Application Priority Data

Apr. 18, 1995 [JP] Japan ................................. 7-115259
Jun. 14, 1995 [JP] Japan ................................. 7-170429

[51] Int. Cl.$^7$ ........................................... C12N 1/20
[52] U.S. Cl. ................. 435/252.1; 435/101; 435/823; 536/56; 536/127
[58] Field of Search ............................. 435/101, 252.1, 435/823; 536/56, 127

[56]    References Cited

U.S. PATENT DOCUMENTS 5,962,277   10/1999   Watanabe et al. ...................... 435/101

OTHER PUBLICATIONS $4^{th}$ International Workshop on Biodegradable Plastics and Polymers, Oct. 11–14, 1995, New England Center, University of New Hampshire, Durham, New Hampshire, USA.
Polymer Preprints, Japan (English Edition), vol. 44 No. 2, SPSJ $44^{th}$ Symposium on Macromolecules Suita, Japan, Sep. 17–19, 1995.
Derwent Abstract 93–269812/34 JP05186501 Sanki Shoji KK "New Polysaccharide NPS . . . ".

*Primary Examiner*—Herbert J. Lilling
*Attorney, Agent, or Firm*—Oblon, Spivak, McClelland, Maier & Neustadt, P.C.

[57]    ABSTRACT

Novel cellulose-producing bacteria including one capable of producing of a bacterial cellulose having a weight-average degree of polymerization in terms of polystyrene of $1.6 \times 10^4$ or above, one capable of producing a bacterial cellulose containing a small amount of the fraction with low degrees of polymerization, one producing a Bingham polysaccharide as a by-product, and one producing a small amount of water-soluble polysaccharide; a method for the production of bacterial cellulose, which comprises culturing these cellulose-producing bacteria; and bacterial cellulose thus obtained.

14 Claims, 7 Drawing Sheets

*FIG. 1*

STRESS CURVE OF WATER-SOLUBLE POLYSACHARIDE

THE EFFECT OF pH ON THE ACTIVITY OF CELLULASE SECRETED BY BPR2001 STRAIN (CMCase)

FIG. 5

THE CHANGE OF A WEIGHT-AVERAGE DEGREE OF POLYMERIZATION
OF BC DURING THE COURSE OF TIME IN CULTIVATION

FIG. 6

THE CHANGE OF THE ACTIVITY OF CMCase
DURING THE COURSE OF TIME IN CULTIVATION

FIG. 7

THE DISTRIBUTION OF THE DEGREE OF POLYMERIZATION
OF BC OBTAINED BY CULTIVATION

CELLULOSE-PRODUCING BACTERIA

This application is a divisional of Ser. No. 08/930,587 filed Jan. 9, 1998 now U.S. Pat. No. 5,962,277 and a divisional of PCT/JP96/00481 filed Feb. 29, 1996.

TECHNICAL FIELD

This invention relates to novel cellulose-producing bacteria including one producing cellulose having high degrees of polymerization, one producing a Bingham polysaccharide as a by-product, and one producing a small amount of water-soluble polysaccharide; a method for the production of cellulosic material (bacterial cellulose: "BC"), which comprises culturing these cellulose-producing bacteria; and bacterial cellulose thus obtained.

BACKGROUND ART

Since the bacterial cellulose is edible as well as tasteless and odorless, it is utilized in the food industry.

The homogenized bacterial cellulose's high dispersibility in water further provides it with many industrial applications, such as to maintain particle sizes of food, cosmetics or coating agents, to strengthen food materials, to maintain moisture, to improve stability of food, and to be used as low-calorie additives and an emulsion stabilizer.

The bacterial cellulose is characterized by a sectional width of its fibrils which is smaller by two orders of magnitude than that of other kinds of cellulose such as those derived from wood pulp.

Due to such structural and physical feature of microfibril, a homogenized bacterial cellulose has plenty of industrial applications as a strengthening agent for polymers, especially hydrophilic polymers. Products prepared by solidification of the homogenized bacterial cellulose in the form of a lump or paper show a high elastic modulus in tension due to the above feature, and are therefore expected to have excellent mechanical properties for use in various kinds of industrial materials.

The methods for the production of BC are disclosed in Japanese Patent Laid-Open Application Sho 62(1987)-265990, Japanese Laid-Open Application Sho 63(1988)-202394 and Japanese Patent Application Publication Hei 6(1994)-43443.

Schramm/Hestrin medium is well known as a nutrient medium suitable for the cultivation of cellulose-producing bacteria, which comprises carbon sources, peptone, yeast-extract, sodium phosphate and citric acid (Schramm et al., J. General Biology, 11, pp.123–129, 1954).

It is also possible to optionally supply accelerators for the cellulose production such as inositol, phytic acid, pyrroloquinoline guinone (PQQ) (Japanese Patent Publication Hei 5(1993)-1718; Mitsuo TAKAI, Japan TAPPI Journal, Vol.42, No.3, pp.237–244), carboxylic acid or their salts (Japanese Patent Laid-Open Application Hei 7(1995)-39386, laid open Feb. 10, 1995), invertase (Japanese Patent Laid-Open Application Hei 7(1995)-184677, laid open Jul. 25, 1995) and methionine (Japanese Patent Laid-Open Application Hei 7(1995)-184675, laid open Sep. 25, 1995) into the culture media. Further, the BC production method with a cultivating apparatus having a specific oxygen-transfer coefficient (KLa) is disclosed in Japanese Patent Application Hei 7(1995)-31787.

Conventionally used culture conditions include static culture, shaken culture, and aerobic agitated culture, and conventionally used culture operation methods include batch fermentation, fed batch fermentation, repeated batch fermentation and continuous fermentation.

Means for agitation include impellers, air-lift fermenters, pump-driven recirculation of the fermenter broth and any combination of these means.

It is well known that the degrees of polymerization of BC are higher than wood pulp (e.g. LBKP and NBKP) and cotton linter used as industrial materials, but lower than a specific cellulose such as that derived from an ascidian and valonia. Polymeric materials including cellulose having higher degrees of polymerization will generally have more excellent mechanical properties such as strength and elasticity. Accordingly, it is expected that the cellulose derived from the ascidian and valonia having high degrees of polymerization is superior in the mechanical properties to the cellulose with low degrees of polymerization.

However, the above specific cellulose such as that derived from the ascidian or valonia has disadvantages that it exists little as resources and can not be efficiently collected, so that it will take much time to produce industrial materials from them. It has been therefore desired to industrially produce the BC having high degrees of polymerization.

Furthermore, it has been found that the BC produced by an industrially advantageous method such as those in an aerobic agitated culture has a lower weight-average degree of polymerization (DPw) than that produced in a static culture. Since the BC with lower degrees of polymerization has been deprived of the excellent mechanical properties, it has been desired to produce the BC having high degrees of polymerization by the aerobic agitated culture method.

It is also known that cellulose-producing bacteria producing no water-soluble polysaccharide as a by-product will show a high BC productivity in the static culture (Journal of General Microbiology (1988), 134, 1731–1736).

On the other hand, it is known that the by-product of water-soluble polysaccharide functions as dispersant in the agitated culture of the cellulose-producing bacteria. Adhesion or catching of BC in the parts of cultivation apparatuses such as impellers and stuffing of these parts with BC may be prevented by its functions so as to form the suspended BC into small clusters. As a result, the BC productivity will be increased (Japanese Patent Laid-Open Application Hei 5(1993)-284988).

The present inventors have now found the bacteria capable of producing BC having high degrees of polymerization or BC containing only a small amount of the fraction with low degrees of polymerization even under the aerobic agitated culture condition, and the bacteria capable of producing only a small amount of water-soluble polysaccharide as the by-product so as to improve in their BC productivity and yield while maintaining the above function of the water-soluble polysaccharide. The present invention is based on these findings.

DISCLOSURE OF INVENTION

The present invention is related to cellulose-producing bacteria capable of producing of a bacterial cellulose having a weight-average degree of polymerization (in terms of polystyrene) of $1.6 \times 10^4$ or above, preferably of $1.7 \times 10^4$ or above, more preferably of $2.0 \times 10^4$ or above.

The weight-average degree of polymerization of a variety kinds of cellulose such as BC of this invention may be determined by the method using a GPC system (Tosoh HLC-8020) equipped with an RI detector as follows:

A cellulose sample is nitrated with a fuming nitric acid-phosphorous pentaoxide solution according to the method of W. J. Alexander, R. L. Mitchell, Analytical Chemistry 21, 12, 1497–1500 (1949).

Nitrated cotton linter is used as a control.

Nitrated cellulose is then dissolved in THF (Wako Pure Chemical Industries Ltd., the first grade) to a final concentration of 0.05%, and filtered through a 1.0 μm pore-size filter. THF is also used for an elution solvent.

The flow rate, pressure, and sample-injection volume are adjusted to be 0.5 ml/min., 10–13 kgf/cm$^2$ and 100 μl, respectively.

The column system consists of two TSKgel GMH-HR (S) columns (7.5 ID×300 mm) and a guard column (Tosoh Co., Ltd.). The analysis is carried out at a temperature of 35° C.

A relative molecular weight in terms of polystyrene is calculated by using polystyrene standards (Tosoh).

The polystyrene standards having a molecular weight in the range of 2.0×10$^7$ to 2630 are used and a standard curve is prepared based on the following three-dimension approximate equation:

$$\log M = At^3 + Bt^2 + Ct + D$$

wherein "t" is an elution time and "M" is a molecular weight.

The weight-average molecular weight and number-average molecular weight are calculated by a program (ver. 3, 10) equipped in a data processor (SC-8020).

The weight-average degree of polymerization and number-average degree of polymerization of the original cellulose samples are finally calculated based on the above data, taking substitution degrees after the nitration into consideration.

The present invention is related to cellulose-producing bacteria producing a Bingham polysaccharide as the by-product.

The "Bingham polysaccharide" means in this specification that an aqueous solution of the polysaccharide shows the same flow property as that of Bingham material, which may be determined by the method described herein below.

The Bingham material does not flow under the shear stress of a specific value ($\tau_f$) or less, but will flow at a shear rate in proportion to the value ($\tau$-$\tau_f$) when the shear stress is increased over the value ($\tau_f$). The "$\tau_f$" is called "Bingham yield value".

The present invention is further related to cellulose-producing bacteria producing a small amount of water-soluble polysaccharide.

The "producing a small amount of water-soluble polysaccharide" means that when the cellulose-producing bacteria are grown under the shaken flask culture conditions as described in Example 1, (3), they will produce a significant amount of less than about 2.1 g/l of water-soluble polysaccharide, or their yield against the consumed sugars (%) will reach less than about 6.7%, at the end of the culture.

Alternatively, it means that when the cellulose-producing bacteria are grown in a jar fermenter culture under the aerobic agitated conditions as described in Example 3, they will produce a significant amount of less than about 4.8 g/l of water-soluble polysaccharide, or their yield against the consumed sugars (%) will reach less than about 6.6%, at the end of the culture.

The amount of water-soluble polysaccharide is determined according to the method described in the present specification.

The present invention is also related to cellulose-producing bacteria capable of producing a bacterial cellulose containing such a small amount as less than about 24% by weight of the fraction with a degree of polymerization of 1,000 or less in terms of polystyrene (referred to hereinafter as the "fraction with the low degrees of polymerization") in the aerobic agitated culture.

The content of the fraction with the low degrees of polymerization is calculated from the % ratio of the area of the same fraction to the total area (100%) on a molecular weight distribution curve prepared by base-line correction of an elution curve obtained with the above data processor.

The present bacteria may be prepared by the treatment for mutagenesis with a known method using mutagens such as NTG (nitrosoguanidine) of Acetobacter strains such as *Acetobacter xylinum* subsp. *sucrofermentans* such as BPR 2001 strain, *Acetobacter xylinum* ATCC23768, *Acetobacter xylinum* ATCC23769, *Acetobacter pasteurianus* ATCC10245, *Acetobacter xylinum* ATCC14851, *Acetobacter xylinum* ATCC11142, *Acetobacter xylinum* ATCC10821; Agrobacterium; Rhizobium; Sarcina; Pseudomonas, Achromobacter; Alcaligenes, Aerobacter; Azotobacter; and Zooglea; followed by the isolation of the strains which have changed in shape and by the determination with the above GPC system of the weight-average degree of polymerization of the bacterial cellulose produced by the thus isolated mutants.

The BPR 2001 has been deposited at the National Institute of Bioscience and Human-Technology, Agency of Industrial Science and Technology (1–3, Higashi 1-chome, Tsukuba-shi, Ibaraki-ken 350 Japan) on Feb. 24, 1993 under accession number FERM P-13466, and then transferred on Feb. 7, 1994 to the deposit under the terms of the Budapest Treaty on the International Recognition of the Deposit of Micro-organisms for the Purposes of Patent Procedure and Regulation under accession number FERM BP-4545.

The chemical mutagenesis treatment using the mutagens such as NTG is described in, for example, Japanese Patent Application Hei 6(1994)-127994, Bio Factors, Vol. 1, pp.297–302 (1988) and J. Gen. Microbiol, Vol. 135, pp.2917–2929 (1989). Accordingly, those skilled in the art may obtain the present mutants in accordance with these known methods. The present mutants may be also obtained by other treatments such as application of radioactive rays.

One example of the present cellulose-producing bacteria, BPR3001A, has been deposited at the National Institute of Bioscience and Human-Technology, Agency of Industrial Science and Technology (1–3, Higashi 1-chome, Tsukuba-shi, Ibaraki-ken 350 Japan) on Jun. 12, 1995 under accession number FERM P-14982, and then transferred on Feb. 23, 1996 to the deposit under the terms of the Budapest Treaty on the International Recognition of the Deposit of Micro-organisms for the Purposes of Patent Procedure and Regulation under accession number FERM BP-5421.

The present invention also relates to a bacterial cellulose having a weight-average degree of polymerization in terms of polystyrene of 1.6×10$^4$ or above, preferably 1.7×10$^4$ or above, which may be produced in the aerobic agitated culture; a bacterial cellulose having a weight-average degree of polymerization in terms of polystyrene of 2.0×10$^4$ or above; and a bacterial cellulose containing less than about 24% by weight of the fraction with the degree of polymerization of 1,000 or less in terms of polystyrene, which may be produced in the aerobic agitated culture.

The present invention is finally related to a method for the production of bacterial cellulose, which comprises culturing these cellulose-producing bacteria; bacterial cellulose thus obtained; and shaped articles made of these bacterial cellulose.

The shaped articles according to the present invention include various industrial materials such as a sheet, fibre and film, which have excellent mechanical properties such as high strength and high elasticity.

Carbon sources in the culture media useful in the present invention include sucrose, glucose, fructose, mannitol, sorbitol, galactose, maltose, erythritol, glycerol, ethyleneglycol, ethanol and their mixtures. In addition, sucrose may be combined with starch hydrolysate containing these carbon sources, citrus molasses, beet molasses, squeezed juice from beet or sugar cane, juice from citrus and the like.

Nitrogen sources useful in the present invention include organic or inorganic ones such as ammonium salts including ammonium sulfate, ammonium chloride, ammonium phosphate; nitrates; and urea. Nitrogen-containing natural nutrients may be also used including Bacto-Peptone, Bacto-soytone, Yeast-Extract and Bean-Condensate.

A trace amount of organic nutrients may be further added including amino acids, vitamins, fatty acids, nucleic acids, 2,7,9-tricarboxy-1H pyrrolo [2,3,5]-quinoline-4,5-dione, sulfite pulp waste liquor, lignin sulfonic acid and the like.

When the mutants with the nutritional requirement for amino acids are used, such required nutrients should be supplemented in the culture media. Inorganic nutrients include phosphate salts, magnesium salts, calcium salts, iron salts, manganese salts, cobalt salts, molybdate salts, hematite salts, chelate metal salts and the like.

It is also possible to optionally supply the above-mentioned accelerators for the cellulose production into the culture media.

For example, when the Acetobacter is used as the cellulose-producing bacteria, a pH range for the culture is controlled between 3 and 7, preferably around 5. A culture temperature is kept in a range between 10 and 40° C., preferably between 25 and 35° C. Oxygen supply into a culturing apparatus may contain from 1 to 100% oxygen, desirably 21 to 80%. Those skilled in the art may optionally determine the contents of these components in the culture media and amounts of the bacteria to be inoculated into the media, depending on the culture method to be used.

The present method may be carried out in the known culture conditions such as the static culture and aerobic agitated culture, as described above.

Means for agitation include impellers, air-lift fermenters, pump-driven recirculation of the fermenter broth and any combination of these means.

Any known culture operation methods such as batch fermentation, fed batch fermentation, repeated batch fermentation and continuous fermentation may be adopted.

Further, the bacterial cellulose may be also produced by the method described in Japanese Patent Laid-Open Application Hei 8(1996)-33494 (laid open Feb. 6, 1996) in the name of the present applicant, wherein culture media containing bacteria are circulated between a culturing apparatus and a separator to separate the resulting bacterial cellulose from the bacteria and culture media in said separator, or by the method described in Japanese Patent Laid Open Application Hei 8(1996)-33495 (laid open Feb. 6, 1996) in the name of the present applicant, wherein the concentration of the bacterial cellulose in culture media is kept at a lower level by a continuous removal of the culture media from its culture system and a continuous supply of fresh culture media having almost the same volume as the removed culture media.

The aerobic agitated culture may be carried out in any culturing apparatus with agitation, such as a jar fermenter and tank.

In the present aerobic agitated culture, gasses may be optionally passed through the culture media. Such gasses include oxygen-containing gases such as air, as well as gasses free of oxygen such as argon or nitrogen. Those skilled in the art may optionally select the gas to be passed, depending on the culture conditions.

For example, when anaerobic bacteria are used, an inert gas may be passed through the culture media so that the bubbles thereof will agitate the culture media.

When aerobic bacteria are used, an oxygen-containing gas may be passed through the culture media to supply oxygen required for the growth of the bacteria. The bubbles thereof will also agitate the culture media.

The bacterial cellulose having less than about 24% by weight of the fraction with the degree of polymerization of 1,000 or less in terms of polystyrene may be produced by other methods than the aerobic agitated culture.

Thus, the bacterial cellulose with a small amount of the fraction of the low degrees of polymerization may be produced by culturing the cellulose-producing bacteria while controlling the activity of cellulase secreted by the same bacteria into the culture media.

For example, endo-cellulase (CMCase) secreted by the cellulose-producing strain, BPR2001, shows a relatively high activity at a pH range of from about 4.5 to about 5.5 with a maximum activity at pH 5. The activity will decrease at lower or higher pH ranges, showing about 10% activity of the maximum one at pH 4 or less. However, the enzyme will never be inactivated even at pH 4 or less.

Accordingly, one specific method for controlling the above cellulase activity may be maintaining the pH of a medium in a range of below about 4.5 or above about 5.5, preferably at about pH 4.

The cellulase activity may be controlled by other ways such as, for example, by limiting other medium conditions such as a salt concentration or by adding an appropriate amount of a reagent capable of inhibiting the cellulase activity into the culture medium.

Further, it is preferred to control the cellulase activity at BC purification and separation steps as well, since the remaining cellulase in the culture medium after the completion of the cultivation can decrease the degree of polymerization of BC. In such case, the cellulase activity may be controlled by any method such as pH limitation, addition of the cellulase inhibitor, heat treatment and alkaline treatment.

The activity of CMCase is determined on the basis of the decrease of viscosity according to J. Biol. Chem. Vol. 250, pp.1012–1018 (1975).

Thus, an enzyme sample (100 $\mu$l) is added to 15 ml of a carboxylmethylcellulose (CMC) solution (0.6%), and the change of viscosity of the mixture is measured during the course of time with a viscometer (Vibro Viscometer CVJ-5000; Chichibu Cement Co. Ltd., Tokyo) at 30° C. An amount of the enzyme which is necessary for causing 1% decrease of the viscosity in 2 h is defined as one activity unit (1 U).

The bacterial cellulose with a small amount of the fraction with the low degrees of polymerization may be produced by other production methods such as, for example, an aerobic agitated culture of the cellulose-producing bacteria with a culture medium containing no corn steep liquor (CSL), culturing the bacteria with water-soluble polysaccharide added in a culture medium and culturing the bacteria producing polysaccharide as the by-product.

The bacterial cellulose according to the present invention may be subjected to homogenization.

The homogenization of the bacterial cellulose is considered to be a phenomenon in which the cellulose is deformed and broken under a stress induced inside the cellulose by an external force such as a mechanical force. Accordingly, the homogenization of the bacterial cellulose may be carried out by externally applying a mechanical force to the bacterial cellulose.

The mechanical force includes tensile stress, bending stress, compressive stress, torsional stress, impact stress and shearing stress. Compressive stress, impact stress and shearing stress are generally dominating.

A practical application of these mechanical forces to the bacterial cellulose may be achieved by using an appropriate apparatus such as a cooking mixer, homogenizer, blender, Polytron or ultrasonic generator.

In the homogenization using the above apparatus, the mechanical force is mainly composed of the impact force generated from the collision between agitating blades and the bacterial cellulose, and of the shearing force generated due to the differences in the speeds of the suspension.

In the homogenization using Polytron, the mechanical force is mainly composed of the compressive force generated by sandwiching the bacterial cellulose between outer blades and inner blades, of the impact force generated from the collision between the bacterial cellulose and blades rotating at a high speed, and of the shearing stress generated in the suspension at a space between stopping outer blades and inner blades rotating at a high speed.

In the homogenization using the ultrasonic generator, the mechanical force is mainly composed of a strong shearing stress locally generated by a continuous cavitation in the suspension due to the oscillation of the ultrasonic generator.

In addition to the above embodiments, the present homogenization may be carried out in any manner for externally applying a certain load (mechanical force) to the bacterial cellulose.

The homogenized bacterial cellulose serving for an excellent emulsifier may be prepared by homogenization of a suspension containing about 1% or less by weight of bacterial cellulose. Those skilled in the art may optionally select the other homogenization conditions.

The bacterial cellulose may be recovered as such, or then impurities other than the bacterial cellulose, including the bacteria per se, may be removed from the recovered bacterial cellulose.

BEST MODE FOR CARRYING OUT THE INVENTION

The present invention will be further illustrated according to the following examples.

EXAMPLE 1

Preparation of Morphological Mutant from BPR 2001

(1) NTG Treatment

A Roux flask (750 ml volume) containing 100 ml of CSL-Fru medium was inoculated with BPR 2001 from glycerol stock, and incubated at 28° C. for 3 days under static culture conditions. After the completion of the culture, the Roux flask was shaken vigorously to release the bacteria cells from the cellulose membrane. The culture was then sterilely filtered through a gauze to obtain a bacteria mixture as filtrate. The resulting bacteria mixture (2 ml) was inoculated into 20 ml of CSL-Fru medium in a flask (100 ml volume) containing 0.2% of cellulose (Meicelase P1; Meiji Seika Kaisha Ltd., Japan), and cultured at 28° C. for 24 hours with shaking of 180 rpm. The culture (10 ml) was inoculated into 10 ml of CSL-Fru medium in a flask (100 ml volume) containing 0.2% of cellulase (Meicelase P1), and grown further for 3 hours under the same shaking conditions. The bacteria suspension was centrifuged at 5,000 rpm for 5 min. and the bacteria cells were washed with 50 mM acid buffer solution (pH 6.5). After the washing, the bacteria cells were resuspended into a phosphate buffer solution (20 ml). 4.5 ml of the resulting suspension was mixed with 0.5 ml of NTG solution (100 μg/ml) and incubated at 30° C. for 30 min. in an assist tube (20 ml volume) with shaking. As a control, a sterilized water (0.5 ml) was used instead of NTG solution. The bacteria cells were collected by centrifugation, and washed with CSL-Fru medium three times. After the washing, the bacteria cells were suspended into CSL-Fru medium (5 ml) containing 0.2% cellulase and cultured at 30° C. for overnight with shaking in order to fix the mutation. 0.1 ml of the suspension was transferred onto a CSL-Fru plate for the measurement of the number of living cells. The same amount of 30% glycerol was added to the culture, and 1 ml of the resulting mixture was transferred into each vial tube for cryopreservation. The survival ratio under the above conditions was about 0.24%.

(2) Isolation of Colony Morphological Mutant

The strains treated with the above mutagen (about 40,000 colonies) were inoculated on YPF plate and grown at 28° C. for about one week.

The morphology of colonies was observed, and 57 colonies showing the different morphology from the parent strain BPR 2001 were selected.

YPF plate

| | |
|---|---|
| Fructose | 40 g/l |
| Yeast Extract | 5 g/l |
| Polypeptone | 5 g/l |
| Agar | 20 g/l |

(3) Selection in Flask Culture

The selected 57 colonies were grown in the following flask culture, and 45 strains showing the decrease of BC productivity were excluded therefrom (The data not shown).

Flask Culture

A Roux flask (750 ml volume) containing 100 ml of the CSL-Fru medium was inoculated at a ratio of 1% from glycerol stock, and incubated at 28° C. for three days in a static culture. After the completion of the culture, the Roux flask was shaken vigorously to release the bacteria cells from the cellulose membrane. The resulting bacteria mixture (12.5 ml) was inoculated into 112.5 ml of CSL-Fru medium in a vertical-type baffle flask (500 ml volume), and cultured at 28° C. for 4 days with shaking of 180 rpm.

(4) Selection Based on Morphological Stability of Colonies

After the static culture for 3 days of the selected 12 strains, they were inoculated on YPF plate and grown at 28° C. for about one week so as to let them form colonies.

The morphology of 100–200 colonies was observed and five strains showing no morphological uniformity were excluded.

BPR 3001A and a8 strains according to the present invention, as well as A26, A6, a12, a53 and a55 strains were finally selected as morphological mutant strains.

EXAMPLE 2

Static Culture of Cellulose-Producing Bacteria and Preparation of BC

A Roux flask (750 ml volume) containing 100 ml of the CSL-Fru medium was inoculated at a ratio of 1% from glycerol stock, and incubated at 28° C. for three days in a static culture. After the completion of the culture, the Roux flask was shaken vigorously to release the bacteria cells from the cellulose membrane. The resulting bacteria mixture (3 ml) was inoculated into 27 ml of CSL-Fru medium in a petri dish (90 mm in diameter), and cultured at 28° C. for 10 days without shaking.

After the completion of the culture, the cellulose membrane produced by the bacteria was washed with flowing water, and heated in about 500 ml of water at 80° C. for 20 min. The cellulose membrane was again washed with flowing water and heated in about 500 ml of 0.1 N NaOH at 80° C. for 20 min. so as to dissolve bacterial cells, followed by washing of the membrane with heating in about 500 ml of distilled water at 80° C. for 20 min. The same washing procedure with the distilled water was repeated three to five times to give a purified BC.

EXAMPLE 3

Aerobic Agitated Culture of Cellulose-Producing Bacteria and Preparation of BC

A Roux flask (750 ml volume) containing 100 ml of CSL-Fru medium was inoculated at 1% ratio from glycerol stock, and incubated at 28° C. for 3 days under the static culture conditions. After the completion of the culture, the Roux flask was shaken vigorously to release the bacteria cells from the cellulose membrane. The resulting bacteria mixture (12.5 ml) was inoculated into 112.5 ml of CSL-Fru medium in a flask (500 ml volume), and cultured at 28° C. for three days with shaking of 180 rpm. The culture contents were aseptically homogenized with a blender, 60 ml of which was inoculated into 540 ml of CSL-Fru medium in a jar (1,000 ml volume), and subjected to a main culture maintaining pH in a range of between 4.9 and 5.1 by means of $NH_3$ gas and 1 N $H_2SO_4$ and keeping the dissolved oxygen (DO) concentration at 3.0% or more by automatically controlling a rotating speed of the impellers.

After the completion of the culture, the resulting culture contents were diluted about 5 times with an acetate buffer solution and centrifuged to collect the pellet. The resulting pellet was diluted about 8 times the volume of the original culture with distilled water, heated at 80° C. for 20 min. and centrifuged so as to collect the pellet. The pellet was suspended into 8 times the volume of the original culture of 0.1 N NaOH and heated at 80° C. for 20 min. so as to dissolve bacterial cells. The resulting lysate was centrifuged, and the collected pellet was suspended into 8 times the volume of distilled water, heated at 80° C. for 20 min. and centrifuged so as to collect the pellet. The same washing procedure with the distilled water was repeated three times to give a purified BC.

The composition of CSL-Fru medium used in the above examples is as follows:

Composition of Culture Medium

TABLE 1

| CSL-Fru medium | |
| --- | --- |
| Fructose | 4.0 (%) |
| $KH_2PO_4$ | 0.1 |
| $MgSO_4 \cdot 7H_2O$ | 0.25 |
| $(NH_4)_2SO_4$ | 0.33 |
| Vitamin Mixture (see below) | 1.0 |
| Salt Mixture (see below) | 1.0 |
| CSL (Corn Steep Liquor) | 2.0 |

TABLE 2

| Vitamin Mixture | |
| --- | --- |
| compound | mg/L |
| Inositol | 200 |
| Niacin | 40 |
| Pyridoxine HCl | 40 |
| Thiamine HCl | 40 |
| Ca Pantothenate | 20 |
| Riboflavin | 20 |
| p-Aminobenzoic Acid | 20 |
| Folic Acid | 0.2 |
| Biotin | 0.2 |

TABLE 3

| Salt Mixture | |
| --- | --- |
| Iron Citrate Ammonium | 1.5 g/L |
| Calcium Chloride | 1.5 g/L |
| Ammonium Molybdate | 0.1 g/L |
| Zinc Sulfate Heptahydrate | 0.2 g/L |
| Manganese Sulfate Tetrahydrate | 0.1 g/L |
| Copper Sulfate Pentahydrate | 2 mg/L |

EXAMPLE 4

Determination of the Degree of Polymerization of Cellulose by GPC

The samples for the determination of the degree of polymerization were prepared as follows:

(1) BC

The bacterial cellulose prepared in Examples 2 and 3 was dried under reduced pressure at 80° C. for 12 hours to give samples for the determination of the degree of polymerization.

As the cellulose-producing bacteria, known BPR 2001 (the parent strain), BPR 1090 (FERM-P12884), BPR 1094 (AJ12725), BPR 1095 (AJ12726), Acetobactor xylinum NCIB 8132 and Acetobactor xylinum NRRL B42 were used as controls, in addition to BPR 3001A, a8, A26 and A6 according to the present invention.

(2) Nata de Coco

Commercially available Nata de coco, such as one from Delmonte (made in Philippines), one imported by Mitsui Bussan Co.(made in Philippines), one prepared by SSK, one prepared by Fujikko Co. and the like, were obtained, and washed and purified in the following way to be subjected to the analysis of the degree of polymerization:

Each Nata de coco (165~220 g) was washed with flowing tap water for three days, soaked in 0.1% acetic acid solution (1,000 ml) for two days and in distilled water for one week, the distilled water being replaced several times for washing, and then autoclaved in 0.1 N NaOH solution (1,000 ml) at 80° C. for 20 min. They were again soaked in distilled water for three days, which was replaced several times for washing, and then autoclaved in distilled water (1,000 ml) at 80° C. for 20 min. These final soaking and autoclaving with distilled water were repeated two times.

They were soaked in distilled water for six days, which was replaced several times for washing, homogenized in the following way to give a suspension of the homogenized Nata de coco.

Each Nata de coco (about 20 g) was mixed with 100 ml of distilled water and the mixture was homogenized by Osterizer at a maximum speed for 2 min. Water of the resulting suspension of the homogenized cellulose was replaced with acetone, and cast-dried on Teflon petri-dish to give a sheet with about 10 μm in thickness.

The resulting four sheets were used as the sample for nitration, which were named Nata de coco #1, Nata de coco #2, Nata de coco #3, and Nata de coco #4, respectively.

Nata de coco imported by Mitsui Bussan Co.(made in Philippines) was also treated with the other washing steps, comprising soaking in tap water for three days and heating in distilled water at 80° C. for 20 min. to give the sample coco #5.

(3) Valonia Cellulose

Valonia ventricosa was washed with water, dried, boiled and washed in 0.1 N NaOH aqueous solution, again washed with water and dried, and then dried under reduced pressure for 12 hours to give a sample for the analysis of the degree of polymerization.

(4) Ascidian Cellulose

An outer coat membrane of Ascidian was sufficiently boiled and washed in 0.1 N NaOH aqueous solution, and washed then with water. It was further washed sufficiently with 2% sodium dodecyl sulfate aqueous solution and washed with water to become white, which was then dried under reduced pressure for 12 hours to give a sample for the analysis of the degree of polymerization.

(5) Plant Cellulose

Cotton linter pulp, hard wood pulp (LBKP, manufactured by Mitsubishi Paper Mills Co.) and soft wood pulp from (NBKP, manufactured by Mitsubishi Paper Mills Co.) were directly subjected to the analysis of the degree of polymerization.

The degree of polymerization of the above samples was determined by the above-mentioned method to give the results in Table 4.

TABLE 4

| Strain | Weight-average degree of polymerization in terms of polystyrene | |
|---|---|---|
| | Static Culture | Aerobic Agitated Culture |
| BPR 3001A | 22500 | 17400 |
| a8 | 22400 | — |
| BPR 2001 | 14900 | 10600 |
| BPR 1090 | 16000 | — |
| BPR 1094 | 19000 | — |
| BPR 1095 | 14000 | — |
| NCIB 8132 | 18800 | — |
| NRRL B42 | 15700 | 8500 |

TABLE 4-continued

| Strain | Weight-average degree of polymerization in terms of polystyrene | |
|---|---|---|
| | Static Culture | Aerobic Agitated Culture |
| A26 | 18300 | |
| A6 | 17000 | |
| Asidian | 26500 | |
| Valonia | 20000 | |
| LBKP | 10000 | |
| NBKP | 12000 | |
| Cotton Linter Pulp | 5300 | |
| Nata de Coco #1 | 14000 | |
| Nata de Coco #2 | 15400 | |
| Nata de Coco #3 | 15800 | |
| Nata de Coco #4 | 14600 | |
| Nata de Coco #5 | 19000 | |

The above Table 4 shows the following points:

1. The weight-average degree of polymerization (DPw) of the bacterial cellulose according to the present invention shows higher values than those of the control bacteria in both the static and aerobic agitated culture conditions.
2. The DPw of BC according to the present invention is higher than that of the cellulose contained in Nata de coco #1–#5.
3. The DPw of BC according to the present invention matches that of the cellulose contained in the asidian and valonia having the high DPw values among naturally occurred celluloses. The DPw of BC according to the present invention is much higher than that of the cotton linter pulp, LBKP and NBKP.

EXAMPLE 5

Analysis of Flow Properties of Water-Soluble Polysaccharide

The culture contents obtained in the aerobic agitated culture were mixed with an equal amount of distilled water, heated at 80° C. for 20 min. and centrifuged to give the supernatant. The pellet was then again extracted with hot water to give the supernatant. Both the supernatants were combined together and filtered through diatomite to give a crude polysaccharide solution without the bacteria cells. To this crude polysaccharide solution was added a twice amount of ethanol to precipitate polysaccharide. The precipitated polysaccharide was collected by filtration through a nylon mesh or by centrifugation. The thus obtained polysaccharide was dissolved in distilled water and dialyzed against distilled water to give a polysaccharide aqueous solution.

The polysaccharide aqueous solution was adjusted by dilution or condensation to a final concentration of 1.6%, which was used for the preparation of a stress curve to give its flow properties.

The stress curve was prepared by measuring the change of the stress for the change of an angle rate with RFS-11 manufactured by Rheometrics Co.

Figure 1:
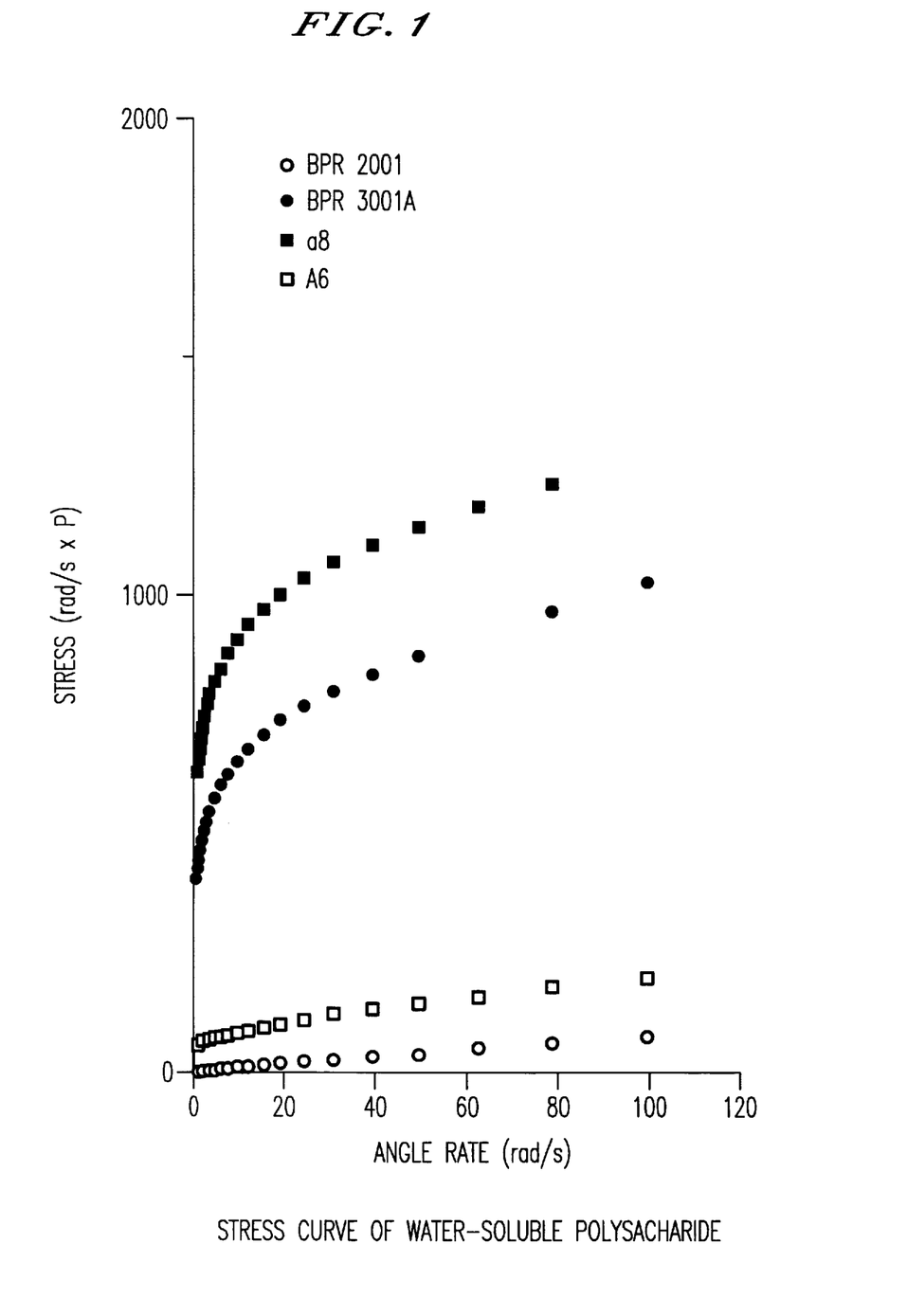
FIG. 1 is a graph showing the stress curve of water-soluble polysaccharide produced by the cellulose-producing bacteria.

FIG. 1 shows the stress curves of the water-soluble polysaccharide produced by BPR 2001, BPR 3001A, a8 and A6. Table 5 shows the values of yield stress and apparent viscosity obtained by the method of least squares from the stress values at 50, 63, 79 and 100 rad/s, respectively. A 26 strain did not produce water-soluble polysaccharide.

TABLE 5

| Strain | Bingham yield value (rad/s × P) | Apparent viscosity (P) |
|---|---|---|
| BPR 2001 | 6.2 | 0.68 |
| BPR 3001A | 710 | 3.1 |
| A6 | 90 | 1.1 |
| a8 | 990 | 2.9 |

While the flow properties of the aqueous solution of water-soluble polysaccharide of BPR 2001 show those of Newtonian flow, the high Bingham yield values of the aqueous solution of water-soluble polysaccharide of BPR 3001A and a8 indicate their Bingham flow properties.

EXAMPLE 6

Production of Water-Soluble Polysaccharide by Cellulose-Producing Bacteria

BPR 2001, a8 BPR, 3001A and A26 strains were grown in flask and jar cultures, respectively, to determine the amount of the water-soluble polysaccharide produced by them. The amount of the water-soluble polysaccharide originally contained in the culture medium (that seems to have been originated from CSL) was also determined.

The flask culture was carried out according to the method of Example 1, (3), and the jar culture was carried out according to the method of Example 3.

After the completion of culture, the culture contents were centrifuged to give the supernatant. The supernatant (0.5 ml) was then mixed with ethanol (1.0 ml) in a 1.5 ml volume plastic tube (Eppendorf) and allowed to stand at −20° C. for 12 hours so that polysaccharide could be precipitated. The precipitated polysaccharide was centrifuged (1,500 rpm, 10 min. 4° C. ) to give the pellet, that was then washed with 70% ethanol. The thus obtained polysaccharide precipitate was dissolved into 1 ml of water and its concentration was appropriately adjusted to serve as a sample for the determination of the amount of polysaccharide. Glucose was used as a standard sample for the above determination. The results are shown in Table 6.

TABLE 6

Accumulated amount of water-soluble polysaccharide and yield of BPR 2001 and its mutants

| | Flask culture | | Jar culture | |
|---|---|---|---|---|
| Strain | Accumulated amount (g/l) | Yield (%) | Accumulated amount (g/l) | Yield (%) |
| BPR 2001 | 2.2 | 6.7 | 5.21 | 6.6 |
| BPR 3001A | 0.39 | 1.3 | 1.25 | 1.2 |
| a8 | 0.36 | 1.0 | 1.19 | 1.0 |
| A26 | 0.07 | 0 | 0.40 | 0 |
| Medium | | 0.08 | | 0.40 |

BPR 2001 produces a considerable amount of water-soluble polysaccharide, as reported in Tonouchi et al., Biosci. Biotech. Biochem., 59, 805–808, 1995. Since A 26 does not substantially produce water-soluble polysaccharide, it may be considered a strain producing no polysaccharide. The amount of water-soluble polysaccharide produced by BPR 3001A and a8 is significantly lower than that of BPR 2001, confirming that these two bacteria belong to the cellulose-producing bacteria producing a small amount of water-soluble polysaccharide according to the present invention.

Yield (Yield against the consumed sugars) (%) was calculated as follows:

$$Y_{PC}=(PS_B-PS_M)/(RC_{MF}-RC_{BF})*100$$

$Y_{PC}$: Yield against the consumed sugars (%)
$PS_M$: water-soluble polysaccharide concentration of the medium (g/L)
$PS_B$: water-soluble polysaccharide concentration of the medium after the culture (g/L)
$RC_{MF}$: Sugar concentration of the medium (g/L)
$RC_{BF}$: Sugar concentration of the medium after the culture (g/L)

EXAMPLE 7

The Amount of BC Production (Accumulation) and Yield of Cellulose-Producing Bacteria BPR 2001, a8, BPR 3001A and A 26 strains were grown in static, flask and jar cultures, respectively, to determine their BC productivity.

The static culture was carried out according to the method of Example 2, with the exception that the main culture was continued for three days using a 250 ml volume Roux flask containing 50 ml of the medium.

The flask culture and jar (1 L) culture were carried out according to Example 1, (3) and Example 3, respectively.

The accumulated amounts of the BC (g/L) in FIG. 7 were calculated as follows. After the completion of the culture, the solid contents in the culture mixture were collected, washed with water to remove the medium components, and treated with 1 N NaOH aqueous solution at 80° C. for 20 minutes to remove the bacterial cells. The resulting cellulose was washed until the washing water became approximately neutral, and dried under vacuum at 80° C. for 12 hours to weigh the dry cellulose. The yield (yield against the consumed sugars) (%) was calculated as follows.
Calculation of Yield against the Consumed Sugars (%)

$$Y_{BC}=BC/(RC_{MF}-RC_{BF})*100$$

$Y_{BC}$: Yield against the consumed sugars (%)
BC: Accumulated amount of BC (g/L)
$RC_{MF}$: Sugar concentration of the medium (g/L)
$RC_{BF}$: Sugar concentration of the medium after the culture (g/L)

TABLE 7

Accumulated amount of BC and yield of BPR 2001 and its mutants

| | Static culture | | Flask culture | | Jar culture | |
|---|---|---|---|---|---|---|
| Strain | Accumulated amount (g/l) | Yield (%) | Accumulated amount (g/l) | Yield (%) | Accumulated amount (g/l) | Yield (%) |
| BPR 2001 | 4.7 | 34.7 | 4.9 | 15.2 | 11.4 | 14.3 |
| BPR 3001A | 5.2 | 49.1 | 6.7 | 28.9 | 18.8 | 25.8 |
| a8 | 4.8 | 49.8 | 6.2 | 22.8 | 15.8 | 20.6 |
| A26 | 6.0 | 46.2 | 4.7 | 18.4 | 2.9 | 11.0 |

Static Culture

A26, the strain producing no water-soluble polysaccharide, has increased the accumulated amount of cellulose and yield, which coincides well with the results described in J. Gen. Microbiol., 134, 1731–1736, 1988.

BPR 3001A and a8, the cellulose-producing bacteria producing a small amount of water-soluble polysaccharide, have also increased the accumulated amount of cellulose and yield.

It seems that the above increases in the accumulated amount of cellulose and yield may be attributed to the decrease or loss of water-soluble polysaccharide.

Agitated Culture

With respect to both BPR 3001A and a8, the cellulose-producing bacteria producing a small amount of water-soluble polysaccharide, the accumulated amount of cellulose and yield have been increased in both the flask and jar cultures.

On the other hand, A26, the strain producing no water-soluble polysaccharide, has produced almost the same accumulated amount of cellulose and yield as its parent strain, BPR 2001 in the flask culture, but has significantly decreased them in the jar culture when compared with their parent strain BPR 2001. It is not clear why the accumulated amount of cellulose and yield have been decreased in the strain producing no water-soluble polysaccharide. However, considering the fact that the parent strain and the cellulose-producing bacteria producing a small amount of water-soluble polysaccharide do not show such phenomena, it may be conceived that the cellulose biosynthesis procedures have become much more susceptible to the agitation due to substantial no production of water-soluble polysaccharide, possibly causing the above decrease.

In the jar culture of A26, the strain producing no water-soluble polysaccharide, it was found that the cellulose would adhere to the inner parts of the jar, preventing the progress in culturing processes. This may be attributed to the fact that the function of water-soluble polysaccharide as a dispersant has been lost due to substantial no production of water-soluble polysaccharide.

Accordingly, it is found that the strain producing no water-soluble polysaccharide is not suitable for the agitated culture in the flask and jar. On the other hand, the cellulose-producing bacteria producing a small amount of water-soluble polysaccharide according to the present invention do not have such disadvantages, and will show a higher cellulose productivity than their parent strain even in the agitated culture.

EXAMPLE 8

Distribution of the Degree of Polymerization of BC

BPR 2001, BPR 3001A and A26 were grown in static and flask cultures and the produced cellulose was evaluated with respect to the distribution of the degree of polymerization.

The static culture was carried out according to the method of Example 2, and the flask culture was carried out according to the method of Example 1, (3). The distribution of the degree of polymerization was obtained by the method mentioned above.

Figure 2:
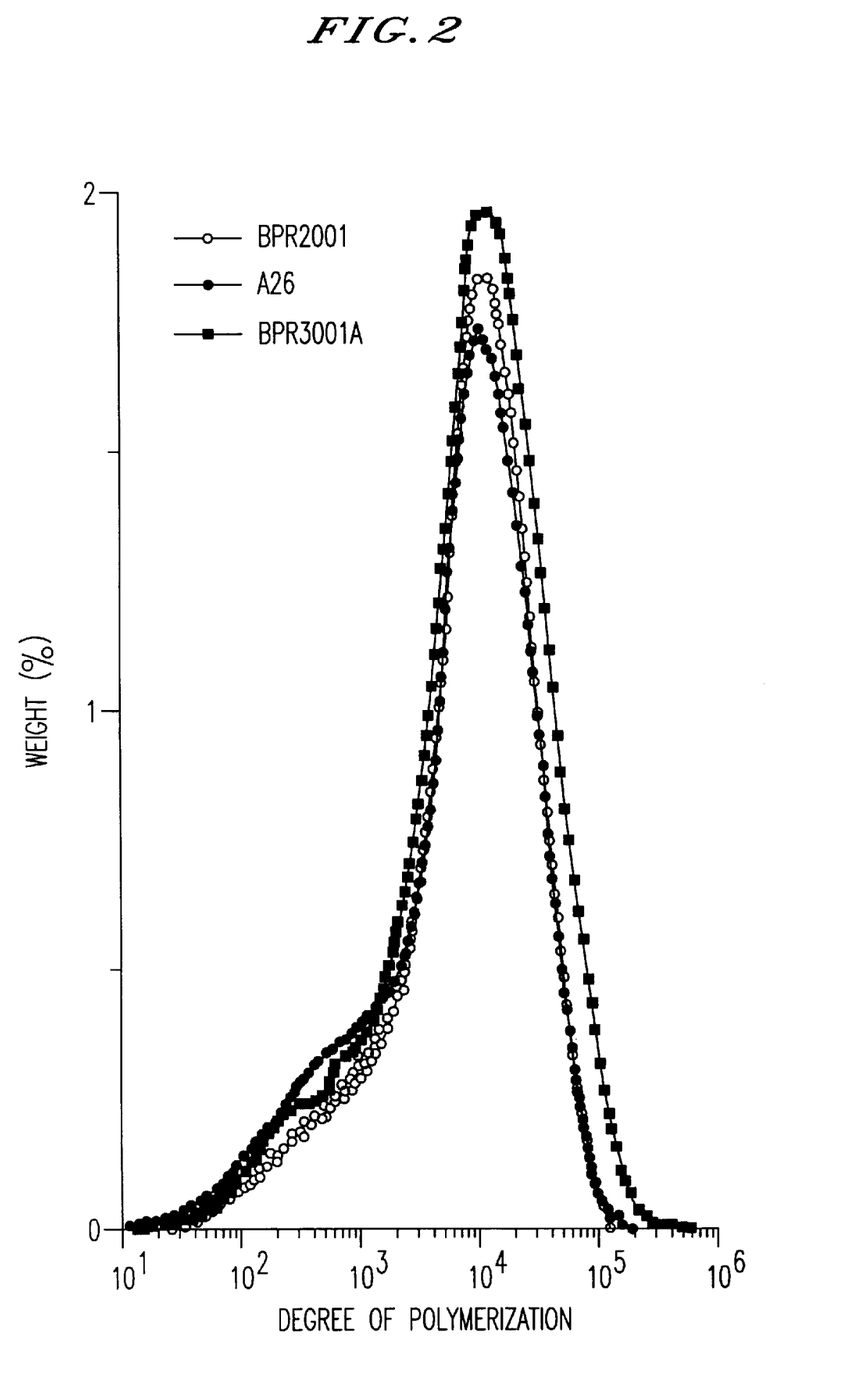
FIG. 2 shows the distribution of the degree of polymerization of BC produced in the static culture.
Figure 3:
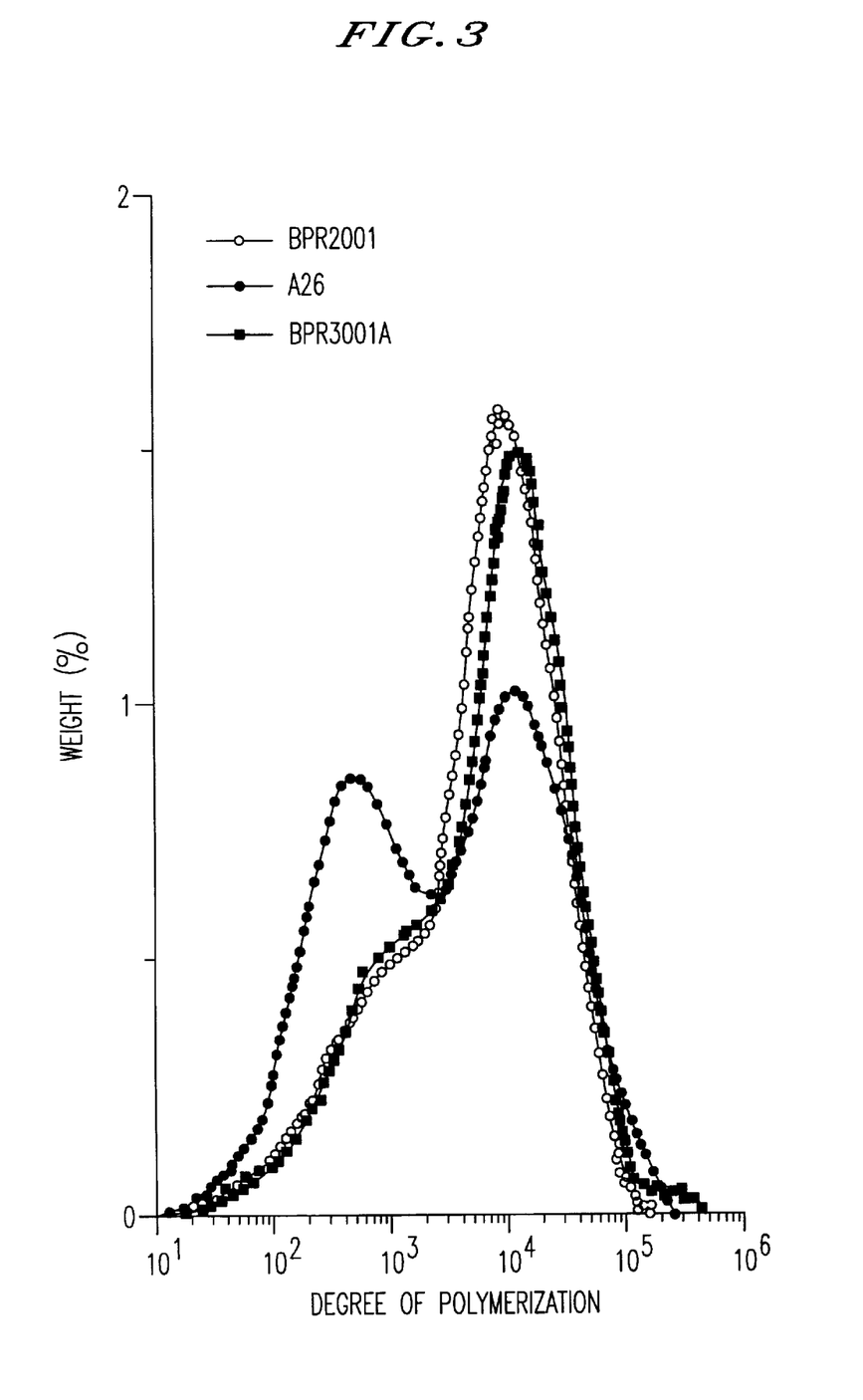
FIG. 3 shows the distribution of the degree of polymerization of BC produced in the flask culture.
Figure 4:
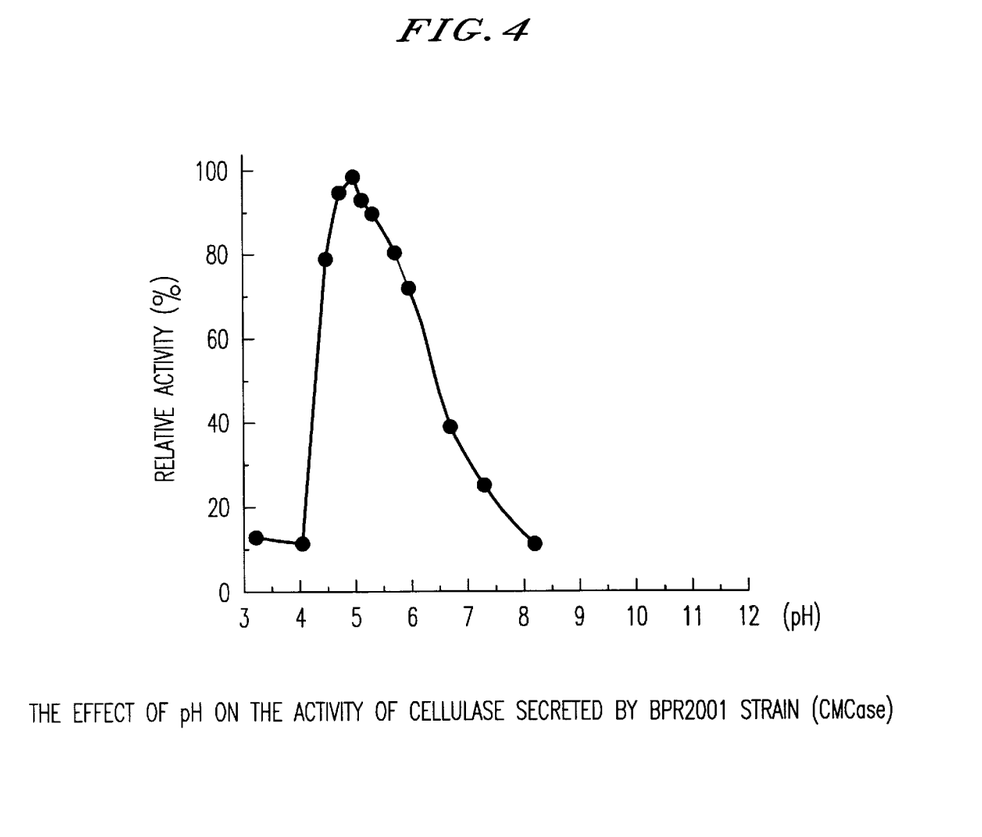
FIG. 4 shows the effect of pH on the activity of cellulase secreted by BPR2001 strain (CMCase).

FIG. 2 and FIG. 3 show the distribution of the degree of polymerization of the cellulose produced in the static and flask cultures, respectively.

A26, the strain producing no water-soluble polysaccharide, has produced a large amount of the BC fraction with the low degrees of polymerization in the flask culture.

By-production of the BC fraction with the low degrees of polymerization in the flask culture is hardly found for BPR 2001. Accordingly, it seems that the loss of the productivity of water-soluble polysaccharide may cause the by-production of the BC fraction with the low degrees of polymerization in the flask culture with agitation.

On the other hand, BPR 3001A, the cellulose-producing bacteria producing a small amount of water-soluble polysaccharide, has produced little amount of the BC faction with the low degrees of polymerization even in the flask culture.

By-production of the cellulose fraction with the low degrees of polymerization is considered to lead to deterioration in the quality of cellulose.

Thus, it is found that the strain producing no water-soluble polysaccharide is not suitable for the agitated culture such as a flask one, in terms of not only productivity but also quality of the produced cellulose.

On the other hand, the cellulose-producing bacteria producing a small amount of water-soluble polysaccharide do not have the above disadvantages, and suitable for the agitated culture, for example, in terms of quality of the produced cellulose.

EXAMPLE 9

Production of BC with a Small Amount of the Fraction with the Low Degrees of Polymerization (1)

BPR 2001, BPR 3001A and ATCC 53263 were grown in the aerobic agitated culture according to Example 3 to produce BC. The degrees of polymerization of the produced BC were determined by the method according to Example 4. From the data on the distribution of the degrees of polymerization, the weight-average degree of polymerization (DPw) was calculated. The ratio of the weight of the fraction with the low degrees of polymerization to the total weight was also obtained. The results are shown in Table 8.

BC produced by BPR 3001A has a higher weight-average degree of polymerization, and a smaller amount of the fraction with the low degrees of polymerization than the other two strains.

TABLE 8

| Strain | DP < 1,000(%) *1 | DPw |
| --- | --- | --- |
| BPR 2001 | 31.0 | 10,600 |
| BPR 3001A | 21.0 | 17,400 |
| ATCC 53263 | 25.0 | 11,200 |

*1: The ratio the weight of the fraction with the degree of polymerization of 1,000 or less in terms of polystyrene to the total weight.

EXAMPLE 10

Production of BC with a Small Amount of the Fraction with the Low Degrees of Polymerization (2)

BPR 2001 was grown in the aerobic agitated culture according to Example 3, using the medium (1) containing as nitrogen source CSL (40 g/L) and Bacto Yeast Extract (7.4 g/L), and the medium (2) containing as nitrogen source ammonium sulfate (7.8 g/L). The degree of polymerization of the thus produced BC was determined in the same manner as Example 9. The results are shown in Table 9.

BC with a higher weight-average degree of polymerization, and a smaller amount of the fraction with the low degrees of polymerization was obtained in the medium (2).

TABLE 9

| Medium | DP < 1,000(%) *1 | DPw |
|---|---|---|
| Medium (1) | 30.1 | 11,800 |
| Medium (2) | 17.8 | 14,600 |

*1: The ratio the weight of the fraction with the degree of polymerization of 1,000 or less in terms of polystyrene to the total weight.

EXAMPLE 11

Production of BC with a Small Amount of the Fraction with the Low Degrees of Polymerization (3)

BPR 2001 was grown in the aerobic agitated culture according to Example 3, controlling the value of pH at 4 and 5. The degree of polymerization of the thus produced BC was determined in the same manner as Example 9. The results are shown in Table 10.

BC with a higher weight-average degree of polymerization, and a smaller amount of the fraction with the low degrees of polymerization was obtained in the culture at pH 4.

TABLE 10

| pH of the Medium | DP < 1,000(%) *1 | DPw |
|---|---|---|
| 5.0 | 28.0 | 11,000 |
| 4.0 | 15.6 | 14,300 |

*1: The ratio the weight of the fraction with the degree of polymerization of 1,000 or less in terms of polystyrene to the total weight.

EXAMPLE 12

Production of BC with a Small Amount of the Fraction with the Low Degrees of Polymerization (4)

A26 was grown in the flask culture according to Example 1, (3), with the addition of water-soluble polysaccharide produced by BPR 2001 of 0%, 0.4%, 0.8%, 1.6% and 3.2%, respectively. The water-soluble polysaccharide was prepared by the method according to Example 5. The degree of polymerization of the thus produced BC was determined in the same manner as Example 9. The results are shown in Table 11.

By the addition of the water-soluble polysaccharide, BC with a smaller amount of the fraction with the low degrees of polymerization was obtained.

TABLE 11

| Amount of the added water-soluble polysaccharide | DP < 1,000(%) *1 |
|---|---|
| 0 | 37.4 |
| 0.4 | 31.1 |
| 0.8 | 27.7 |
| 1.6 | 24.6 |
| 3.2 | 23.6 |

*1: The ratio the weight of the fraction with the degree of polymerization of 1,000 or less in terms of polystyrene to the total weight.

EXAMPLE 13

Preparation of a Sheet and its Properties

Young's modulus and tensile strength were measured with respect to a sheet made of the homogenized BC which had been obtained in Examples 2, 3 and 11, and summarized in Table 12 and Table 13.

It is found from these tables that the sheet made of the homogenized BC with the high weight-average degree of polymerization shows high Young's modulus and tensile strength values. The tables also show that the sheet made of the homogenized BC containing a small amount of the fraction with the low degrees of polymerization shows high Young's modulus and tensile strength values.

Thus, BC with the high degree of polymerization or containing a small amount of the fraction with the low degrees of polymerization can provide industrial materials with high strength and high elasticity.

The homogenized BC was prepared as follows:

The homogenization was carried out by means of a conventional homogenizer with a blade at 18,000 rpm for one min. in 2.00 ml suspension with a concentration of 0.5%. The homogenized suspension was diluted with pure water to a final concentration of 0.2~0.5% in terms of a dried BC, and air was sucked under vacuum. The resulting BC was transferred to the extent of about 8 mm in depth into an acrylic petri-dish (5 cm in diameter) placed horizontally and dried at 50° C. for about 5 hours. The sheet adhering to the petri-dish was carefully released.

A strip (5×30 mm) sample was cut out of the above-prepared sheet. After measuring its weight and thickness, Young's modulus was determined by means of a dynamic viscoelasticity measuring apparatus (DMS210) manufactured by SEIKO Electric Industry Co. The measurement was carried out by an automatic tension method with an initial tension of 4,000 g/mm$^2$, fluctuation amount±20 $\mu$m, and frequency of 10 Hz and with an increase of temperature to give tensile storage modulus (Young's modulus) and internal loss. The maximum value in the temperature dispersion pattern of Young's modulus (a temperature range of between 28° C. and 75° C.) was considered Young's modulus in an absolutely dry state. The cross area of the sample was calculated from the thickness and width. True Young's modulus was calculated from the above tensile storage modulus, using a constant density of cellulose of 1.58.

The tensile strength of the homogenized BC sheet having 20 mm in length was measured by using a rheometer (NRM-2010J-CW) manufactured by Fudo Manufacturing Co. with a tension rate of 2 cm/min.

TABLE 12

| Strain | BPR 3001A | BPR 2001 | |
|---|---|---|---|
| Young's Modulus (GPa) | 34.5 | 33.5 | Example 2 |
| | 31.0 | 28.0 | Example 3 |

TABLE 13

| Sample | Young's Modulus (GPa) | Tensile Strength (MPa) |
|---|---|---|
| BC Culture at pH 5 | 28.0 | 51.0 |
| BC Culture at pH 4 | 31.6 | 58.0 |

EXAMPLE 14

Aerobic Agitated Culture of Cellulose-Producing Bacteria and Structure and Properties of the Obtained BC BPR 2001 was inoculated into a flask (500 ml volume) with baffles containing 125 ml of CSL-Fru medium and grown at 28° C. for three days with shaking.

The total volume of the bacteria mixture was added to a jar (3 L volume) containing 2 L of CSL-Fru medium. A main culture was carried out with an aeration rate of 660 ml/min. and an agitation rate of from 400 to 1,200 rpm, so that a necessary amount of the dissolved oxygen could be fulfilled. The pH was adjusted to 4 or 5.

Figure 5:
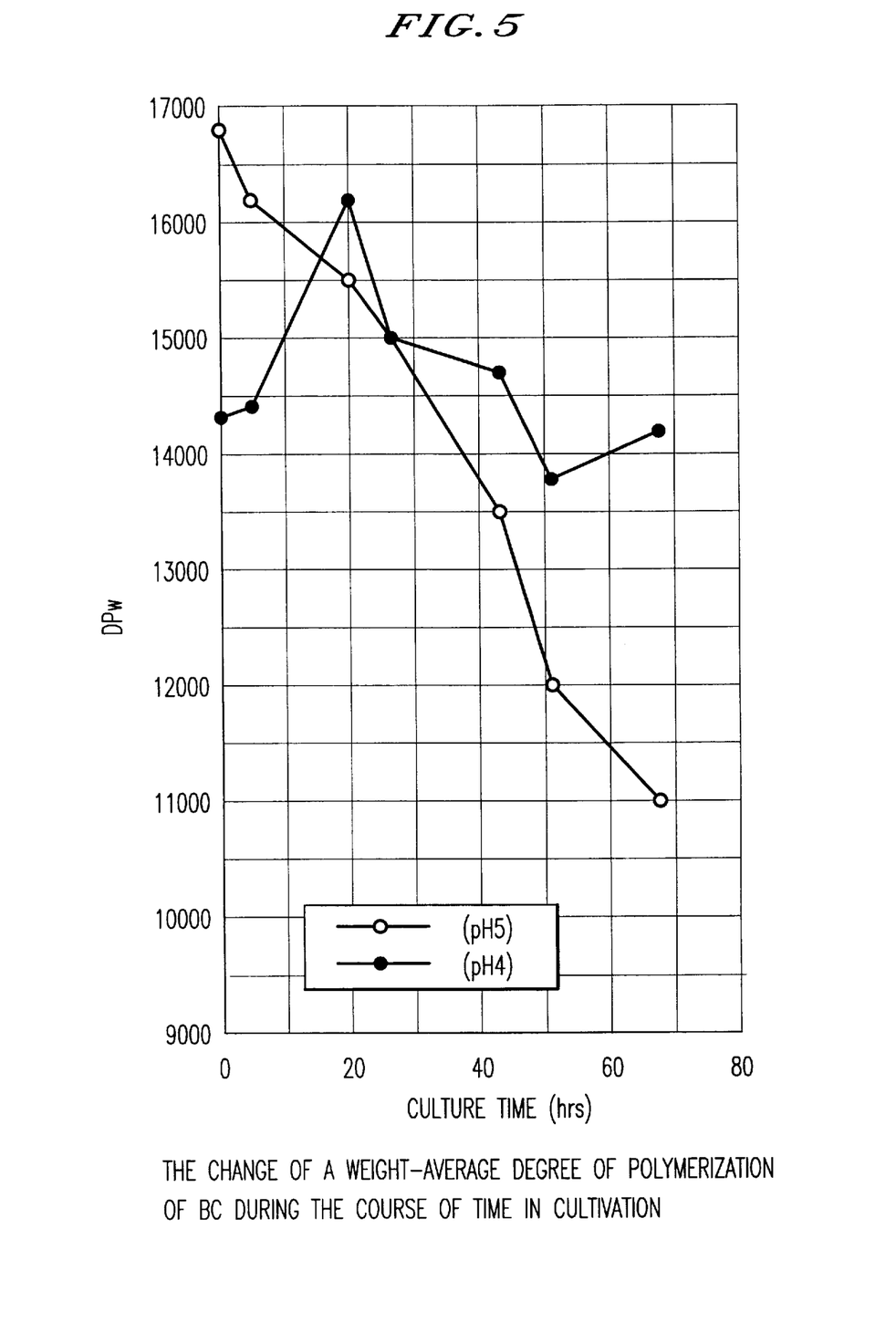
FIG. 5 shows the change of a weight-average degree of polymerization of BC during the course of time in cultivation.
Figure 6:
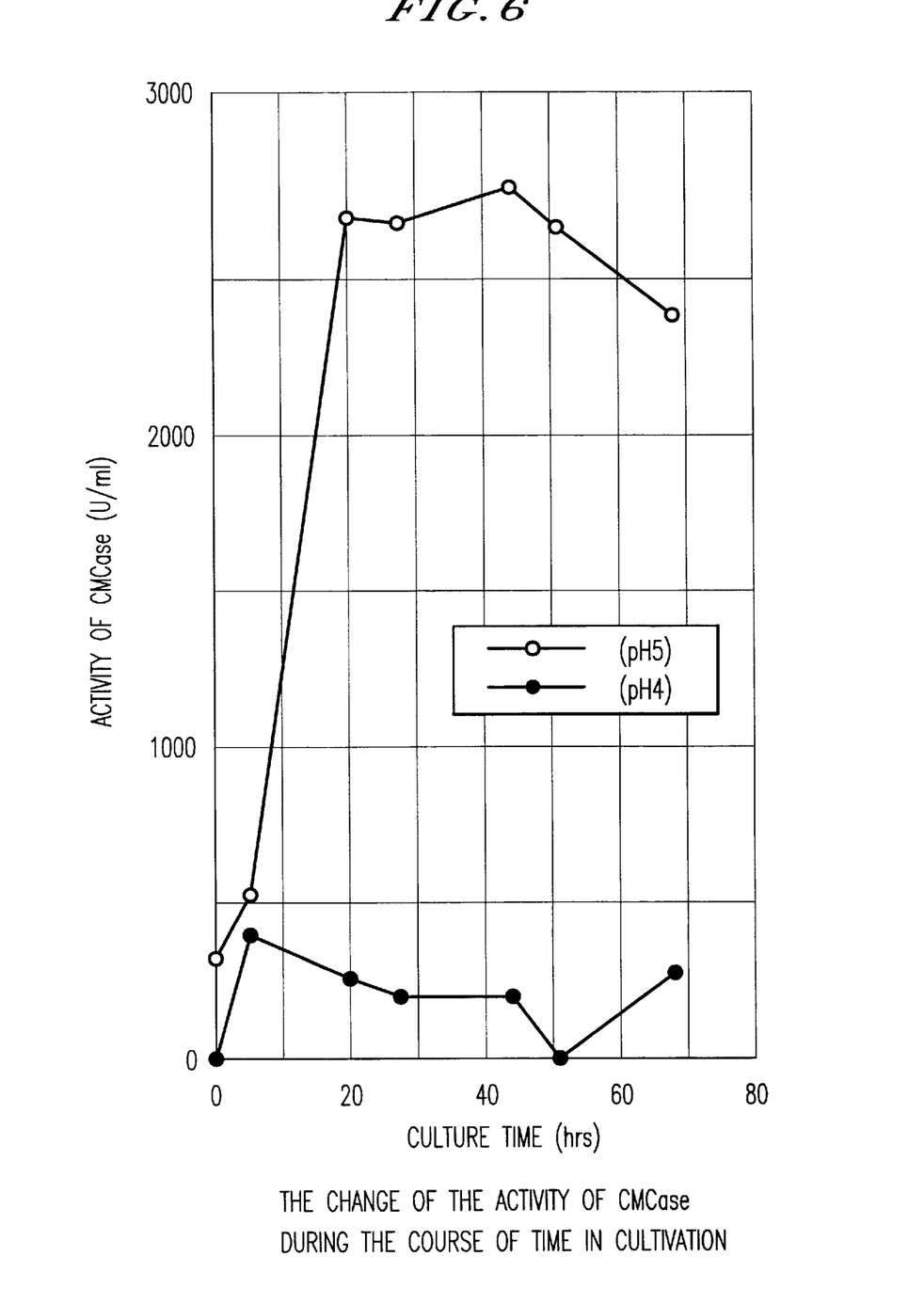
FIG. 6 shows the change of the activity of CMCase during the course of time in cultivation.

The change of the weight-average degree of polymerization and the activity of CMCase during the course of time were shown in FIG. 5 and FIG. 6.

These results show that by maintaining the pH of the medium at 4, the activity of CMCase was reduced to a significant extent (to about 10% of that at pH 5) to give BC with a high weigh-average degree of polymerization.

The weight-average degree of polymerization of BC was determined by the method using a GPC system (Tosoh HLC-8020) equipped with an RI detector as mentioned before.

The structure and properties of the BC obtained in the culture at pH 4 (pH4BC) and pH 5 (pH5BC) were examined and compared with each other by the distribution of degrees of polymerization (FIG. 7), and X-ray diffraction and $^{13}$C-NMR analysis (Table 14).

The X-ray diffraction and $^{13}$C-NMR analysis were carried out as follows:

Determination of Degree of Crystallinity and Crystal Size by X-ray Diffraction

BC purified and washed as mentioned before was lyophilized, shaped into a plain tablet under a pressure of 200 kg/cm$^2$ and to be subjected to X-ray diffraction.

The resulting peaks were separated by the method of least squares on the assumption that the extension of the peaks may be approximated with Gauss function based on X-ray diffraction curve (reflection method) at a diffraction angle (2θ) of 5°~40°. The ratio of the area of the resulting crystal diffraction peak to the total scattering intensity was taken as degree of crystallinity. The crystal size in the direction perpendicular to each of three crystal faces was calculated from the width at half the crystal diffraction peak according to Scherrer's equation. The crystal face was indexed according to cellulose Iβ of two-chain single crystal.

Determination of Degree of Crystallinity with Solid NMR

BC purified and washed as mentioned before was lyophilized, added with an equal amount of water and to be subjected to solid NMR. Separation analysis of a wave shape was carried out according to the method of Horii et al. (H. Yamamoto, F. Horii and H. Odani, Macromolecules, 22, 4180 (1989)) with respect to the peaks attributed to C$_4$ of a glucose residue in the spectra obtained with CP/MAS $^{13}$C-NMR to give degree of crystallinity.

TABLE 14

Comparison of degree of crystallinity and crystal size by X-ray diffraction and $^{13}$C-NMR analysis of pH4BC and pH5BC

|  | X-ray | | | $^{13}$C-NMR |
| --- | --- | --- | --- | --- |
|  | Crystal (nm) | size | Degree of Crystallinity (%) | Degree of Crystallinity (%) |
|  |  | face |  |  |
| pH5 BC | 6.859 | (110) |  |  |
|  | 8.604 | (110) | 71.0 | 72.75 |
|  | 8.198 | (200) |  |  |
| pH4 BC | 7.080 | (110) |  |  |
|  | 8.969 | (110) | 75.5 | 76.35 |
|  | 8.391 | (200) |  |  |

Figure 7:
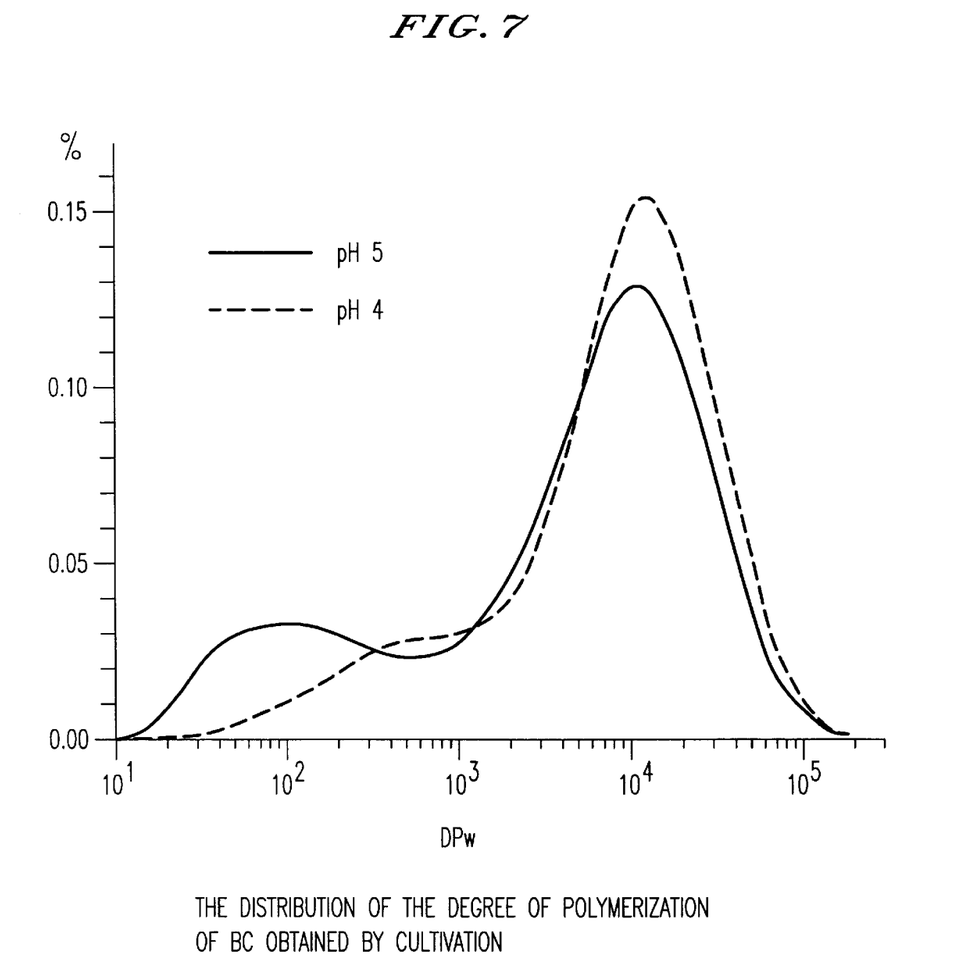
FIG. 7 shows the distribution of the degree of polymerization of BC obtained by cultivation.

The above results show that pH4BC, when compared with pH5BC, has lost the fraction with the low degrees of polymerization, as obtained by the distribution curve of the degrees of polymerization, and the fraction with the high degrees of polymerization of pH4BC has shifted further to higher degrees of polymerization (FIG. 7).

The X-ray diffraction and $^{13}$C-NMR analysis demonstrate that the crystal size and degree of crystallinity of pH4BC are higher than those of pH5BC, as shown in Table 14.

Industrial Applicability

The present invention has made it possible to produce the bacterial cellulose with the high degrees of polymerization or containing the small amount of the fraction with the low degrees of polymerization with a high yield.

Such BC may provide industrial materials with high strength and elasticity. A solution of the present BC in an appropriate solvent will have high viscosity. It is also expected that the shaped articles of regenerated cellulose such as fibers and films, which are prepared from the above solution will show excellent mechanical properties.

What is claimed is:

1. A bacterial cellulose containing less than about 24% by weight of the fraction with a degree of polymerization of 1,000 or less in terms of polystyrene, which may be produced in an aerobic agitated culture.

2. A method for the production of the bacterial cellulose according to claim 1, which comprises culturing a bacteria which produces said bacterial cellulose in an aerobic agitated culture.

3. A method for the production of the bacterial cellulose according to claim 1, which comprises culturing cellulose-producing bacteria in an aerobic agitated culture while controlling the activity of cellulase secreted by the cellulose-producing bacteria.

4. A method for the production according to claim 3, which comprises maintaining the pH of a medium at about 4.

5. A method for the production of the bacterial cellulose according to claim 1, which comprises culturing cellulose-producing bacteria in an aerobic agitated culture with a medium not containing corn steep liquor.

6. A method for the production of the bacterial cellulose according to claim 1, which is an aerobic agitated culture in the presence of water-soluble polysaccharide.

7. A bacterial cellulose which is produced according to the method of claim 2.

8. A shaped article made of the bacterial cellulose according to claim 7.

9. A bacterial cellulose, produced according to the method of claim 3.

10. A bacterial cellulose, produced according to the method of claim 4.

11. A bacterial cellulose, produced according to the method of claim 5.

12. A bacterial cellulose, produced according to the method of claim 6.

13. A shaped article made of the bacterial cellulose according to claim 1.

14. A shaped article made of the bacterial cellulose according to claim 9.

* * * * *